United States Patent
Axelgaard

(10) Patent No.: US 7,697,999 B2
(45) Date of Patent: *Apr. 13, 2010

(54) MOISTURE RESISTANT ELECTRODE WITH EDGE PROTECTION

(75) Inventor: Jens Axelgaard, Fallbrook, CA (US)

(73) Assignee: Axelgaard Manufacturing Company, Ltd., Fallbrook, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 11/588,539

(22) Filed: Oct. 27, 2006

(65) Prior Publication Data

US 2007/0043417 A1    Feb. 22, 2007

Related U.S. Application Data

(63) Continuation-in-part of application No. 11/519,676, filed on Sep. 11, 2006, which is a continuation-in-part of application No. 11/335,990, filed on Jan. 20, 2006, which is a continuation-in-part of application No. 10/359,988, filed on Feb. 6, 2003, now Pat. No. 7,324,847.

(51) Int. Cl.
*A61N 1/04* (2006.01)
(52) U.S. Cl. ............... 607/142; 600/372; 600/374
(58) Field of Classification Search ........... 600/382, 600/384, 393; 607/142
See application file for complete search history.

(56) References Cited

U.S. PATENT DOCUMENTS

| | | | |
|---|---|---|---|
| 5,269,810 A * | 12/1993 | Hull et al. | 607/129 |
| 5,727,550 A | 3/1998 | Montecalvo | |
| 5,785,040 A | 7/1998 | Axelgaard | |
| 6,148,233 A | 11/2000 | Owen et al. | |
| 6,600,957 B2 * | 7/2003 | Gadsby | 607/142 |
| 6,687,524 B1 | 2/2004 | Svejk | |
| 6,795,722 B2 | 9/2004 | Sheraton et al. | |
| 6,950,688 B2 | 9/2005 | Axelgaard et al. | |
| 7,078,582 B2 * | 7/2006 | Stebbings et al. | 602/57 |
| 2006/0173523 A1 | 8/2006 | Rainey et al. | |

OTHER PUBLICATIONS

Webster's Ninth New Collegiate Dictionary (Springfield, Massachusetts, 1990), 443.*

* cited by examiner

*Primary Examiner*—Carl H Layno
*Assistant Examiner*—Frances P Oropeza
(74) *Attorney, Agent, or Firm*—Walter A. Hackler

(57) ABSTRACT

A medical electrode includes a conductive flexible member having a top side and a bottom side with a connector in contact with a flexible member for establishing electrical contact with an external apparatus. An oversize non-conductive flexible sheet covering the conductive flexible member top utilizes concentric adhesives. A conductive hydrogel adhesive disposed on the conductive flexible member bottom side for adhering the electrode to a patient's skin.

5 Claims, 2 Drawing Sheets

MOISTURE RESISTANT ELECTRODE WITH EDGE PROTECTION

The present application is a continuation-in-part of U.S. Ser. No. 11/519,676 filed Sep. 11, 2006 which is a continuation-in-part of U.S. Ser. No. 11/335,990 filed Jan. 20, 2006, which is a continuation-in-part of U.S. Ser. No. 10/359,988 filed Feb. 2, 2003, now U.S. Pat. No. 7,324,847. These referenced patent applications are to be incorporated herein in toto by this specific reference thereto.

The present invention generally relates to electrodes and, more particularly, electrodes suitable for transcutaneous nerve and/or muscle stimulation and biological signal recording.

Medical electrodes must provide an even electrical distribution to a patient's skin over an entire surface of the electrode to assure proper coupling. Because of the curvaceous nature of the human body, it is apparent that medical electrodes for use thereon must be flexible not only for conformation with a patient's skin contours, but also to accommodate relative movement of the patient's skin.

It is well known that inadequate flexing and shaping of the electrode to a patient's contour can result in irritation of the patient's skin. Electrical "hot spots" due to uneven electrode-skin contact can result in a rash or a burning sensation. A sensation of burning may be felt by a patient within a few minutes after application of the electrical signals during nerve and/or muscle stimulation, while rash conditions generally take a longer period of time to develop.

In order to provide uniform electrical coupling, heretofore developed electrodes have utilized conductive fabrics and foils in combination with a conductive and flexible adhesive in order to uniformly couple electrical signals to and/or from an electrical lead wire, or connector.

A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, and U.S. Pat. No. 5,904,712 CURRENT CONTROLLING ELECTRODE to Axelgaard. U.S. Pat. No. 4,736,752 teaches the control of current density across an electrode through the use of conductive ink design areas. These patents are incorporated in their entirety herewith by this specific reference thereto.

Many prior art electrodes have compromised the flexibility of the electrode in order to provide adequate current densities over the entire contact area of the electrode. Such electrodes typically have utilized a metallic mesh, or foil, to provide conductivity and utilize a conductive gel between the electrode and the patient's skin in order to accommodate the movement therebetween. Such use of foil or mesh often cause burning or hot spots at electrode edges.

A common prior art problem with medical electrodes using a conductive adhesive is the leakage of electrical current from edges of the conductive adhesive, or gel, which is known in the art as edge biting. In addition, exposed adhesive, or gel, has a tendency to dry upon exposure to air and, in addition, entry of foreign material to the gel is possible because of the adhesive nature thereof.

A further problem with most prior art electrodes is the fact that the conductive hydrogels utilized to contact the electrode with a patient's skin are hydrophilic and therefore lose their adhesiveness when satiated with water. Thus, when such electrodes are utilized to monitor a patient for a relatively long period of time, absorption of water causes erosion of the adhesiveness of the hydrogel.

This problem is particularly acute in high humidity environments such as, for example, in neonatal incubators.

The present invention addresses these problems with prior art electrodes by preventing contact of a conductive member with a patient's skin and also providing a moisture resistant seal for the conductive adhesive.

SUMMARY OF THE INVENTION

A medical electrode in accordance with the present invention generally includes a conductive flexible member having a top side and a bottom side along with a connector in contact with the conductive flexible member for establishing electrode contact with an external apparatus.

A non-conductive flexible sheet is disposed over the conductive flexible member top side with the non-conductive flexible sheet having dimensions greater than the conductive flexible member causing an overlap thereof by a sheet perimeter.

A central adhesive may be provided for bonding the non-conductive flexible member to the top side of the conductive flexible member and securing a connector to the conductive flexible member top side and a perimeter adhesive may be disposed about said central adhesive on the sheet perimeter and enabling moisture resistant sealing of the electrode to a user's skin as will be hereinafter discussed in greater detail.

A conductive adhesive is provided and disposed on the conductive flexible member bottom side in a spaced apart relationship with the perimeter adhesive for adhering the electrode to a patient's skin. This spacing further prevents moisture contact with the conductive adhesive. Preferably, the conductive adhesive is a hydrogel and the perimeter adhesive is a silicone adhesive.

An improvement in accordance with the present invention is directed to the non-conductive flexible sheet disposed over the connector on the conductive flexible member top side. As hereinabove noted, the dimensions of the non-conductive flexible sheet are greater than the conductive flexible member thereby causing an overlap in order to prevent contact of the conductive member with a user's skin and further to provide a seal for the conductive adhesive. A perimeter adhesive is provided, surrounding the central adhesive and enabling moisture resistant sealing of the electrode to a user's skin.

In another embodiment of the present invention, a medical electrode includes a plurality of spaced apart conductive flexible members having top sides and bottom sides along with a plurality of connectors with each connector in contact with a corresponding conductive flexible member for establishing electrical contact with an external apparatus.

A non-conductive flexible sheet is provided and disposed on the conductive flexible member with the non-conductive flexible sheet having dimensions greater than a total dimension of the conductive flexible members thereby causing an overlap thereof by a sheet perimeter.

A plurality of central adhesives may be provided for bonding the conductive flexible members to the non-conductive flexible sheet and to secure the connectors to the corresponding connective flexible members. A perimeter adhesive is disposed about the plurality of central adhesives, on the sheet perimeter which enables moisture resistant sealing of the electrode to a user's skin. A conductive adhesive is disposed on the conductive flexible member bottom sides, in a spaced apart relationship with the perimeter adhesive, for adhering the electrode to a patient's skin.

BRIEF DESCRIPTION OF THE DRAWINGS

The present invention may be better understood with reference to the following detailed description when taken in conjunction with the accompanying drawings, in which.

DETAILED DESCRIPTION

Figure 1:
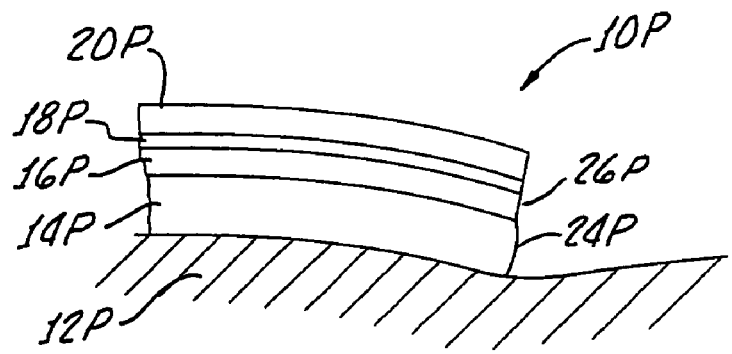
FIG. 1 is a cross sectional view of a prior art electrode as disposed on a user/patient skin generally including a non-conductive sheet, adhesive layer, conductive member, and conductive adhesive.
Figure 1A:
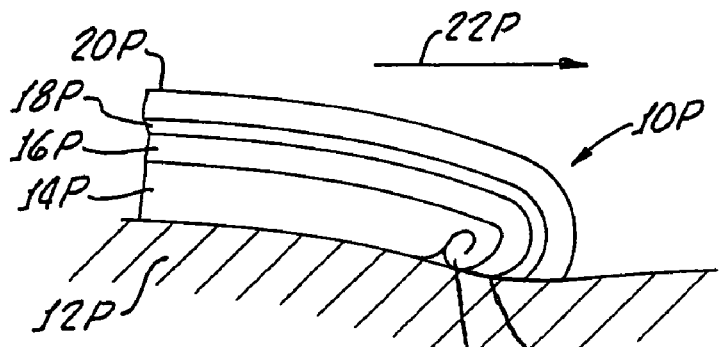
FIG. 1a is a cross sectional view of the electrode shown in FIG. 1 illustrating contact of the conductive member with the skin upon rolling of the electrode due to an external force applied thereto.
Figure 1B:
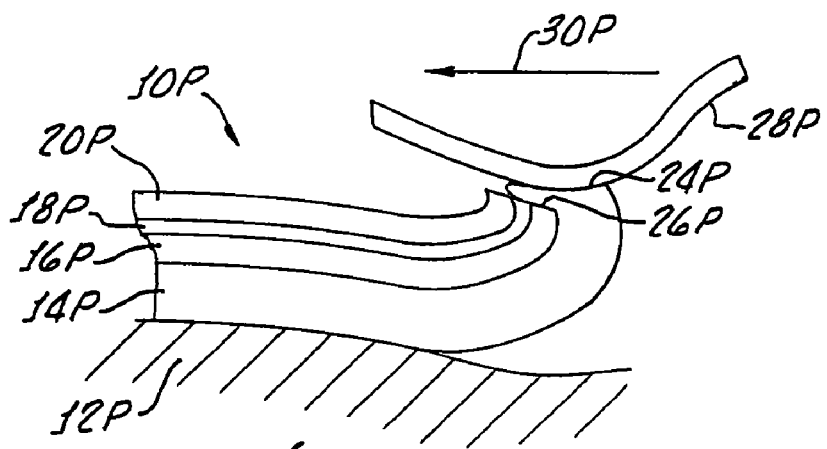
FIG. 1b is a cross sectional view of the prior art electrode shown in FIG. 1 illustrating dislodgement of the electrode from the user's skin due to the action of clothing being brushed thereagainst.

With reference to FIGS. 1, 1a, and 1b, there is shown a prior art electrode 10P shown disposed on a patient's/user's skin 12P and generally including a conductive adhesive 14P, a conductive member 16P, an adhesive layer 18P, and a non-conductive sheet 20P.

FIG. 1 illustrates the electrode 10P upon initial placement onto the skin 12P. However, as illustrated in FIG. 1A, the electrode 10P when subjected to a movement of the non-conductive sheet, as illustrated by the arrow 22P causes a rolling of the electrode 10P with a curling of an end 24P thereby causing contact of an end 26P of the conductive member 16P enabling or causing a burning sensation in the skin 12P.

A further disadvantage of the prior art electrode 10P, as illustrated in FIG. 1B, because the adhesive end 24P is exposed, it can contact, and adhere, to an article of clothing 28P and upon movement of the clothing 28P, as shown by the arrow 30P, the electrode 10P can be partially lifted from the skin 12P, thus significantly reducing the effectiveness of the electrode 10P.

Figure 2:
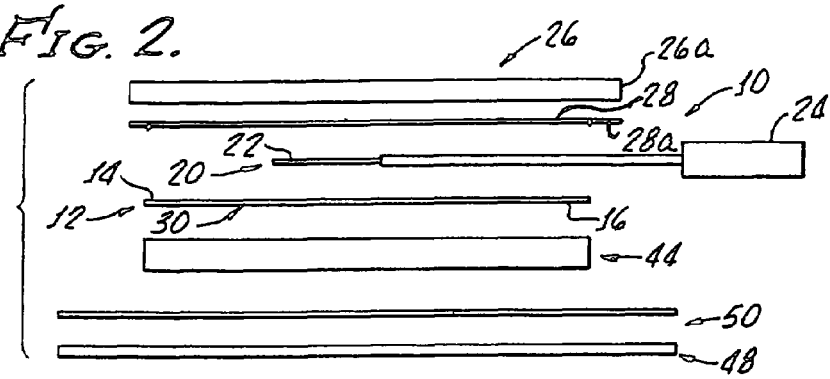
FIG. 2 is an exploded cross sectional view of a medical electrode in accordance with the present invention generally showing a conductive fabric having a top and a bottom side, a connector in contact with the member top side, and a non-conductive flexible sheet covering the conductive flexible member with the sheet having dimensions greater than the conductive member and conductive adhesive causing an overlap, a central adhesive for bonding the nonconductive flexible sheet to the top side of the conductive flexible member and a perimeter adhesive disposed about he central adhesive, on the sheet perimeter, enables sealing of electrode to a user's skin (not shown)
Figure 3:
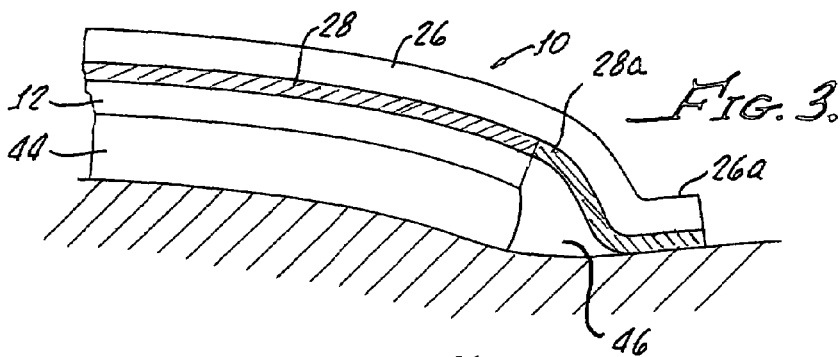
FIG. 3 is an exploded cross sectional view of an edge of the assembled electrode illustrated in FIG. 2 applied to a patient's skin and illustrating the prevention of contact of the conductive member with the skin by adhesion of the non-conductive flexible sheet directly to the skin by the perimeter adhesive which is spaced apart from the conductive adhesive.

These disadvantages of the prior art electrode 10P are overcome by the electrode 10 in accordance with the present invention as illustrated in FIGS. 2 and 3 which generally includes a conductive flexible member 12 having a top side 14 and a bottom side 16.

The conductive flexible member may be a conductive fabric and is described in U.S. Pat. No. 4,722,354 and U.S. Pat. No. 4,708,149 to Axelgaard and these references are to be incorporated herein in their entirety for providing a description of the flexible conductive fabric.

A connector 20, which may include a lead wire 22 and jack 24 is provided with a lead wire 22 in contact with the member top side 14.

A non-conductive flexible oversize sheet 26 covers the conductive flexible member 12 along with the connector 20 and the sheet 26 may be adhered to the flexible member 12 with a central adhesive layer 28 which also holds the lead wire 22 in contact with the member 12. The adhesive 28 is preferably a hot melt glue made by Bostick Findley, Borden or 3M. Moisture is prevented by sealing the central adhesive 28 and conductive adhesive 44 by a concentric perimeter adhesive 28a, as hereinabove noted.

Importantly, sheet 26 has dimensions greater than overall dimensions of the member 12 resulting in an edge, or perimeter, 26a which overlaps the member 12, see FIG. 3. This structure eliminates the need for alignment of the sheet 26 with the member along their peripheries as with the prior art. The perimeter adhesive 28a covers the edge 26a and is preferably a soft skin silicone adhesive available from DOW Corning. This adhesive is non hydrophilic and consequently provides a moisture resistant seal which is particularly important in high humidity environment such as neonatal incubators.

The oversized sheet 26 enables the electrode 10 to be sealed along the perimeter 26a to a user's skin and stabilizes the electrode in a vertically aligned configuration to prevent "rolling" action of the prior art electrode 10P, shown in FIG. 1a and 1b. This, in turn, enables activity by a user and further enables bathing or showering by the user without degradation of the electrode/skin coupling. Water is prevented from entering the electrode 10 under the sheet 26 by the perimeter adhesive 28a.

The lead wire 22 may be of any suitable conductive material.

With reference again to FIG. 2, a conductive hydrogel adhesive 44, may be utilized for adhering the electrode 10 to a patient's skin, not shown. A suitable adhesive is described in U.S. Pat. No. 6,038,464. In addition, because the sheet edge 26a and perimeter adhesive 28a are spaced apart from the hydrogel adhesive 44, a gap 46 further prevents environmental contamination with the hydrogel adhesive 44.

A plastic, paper, or other suitable carrier 48 along with a release coating 50 may be provided in order to prevent inadvertent and/or premature adhesion of the patients' skin or other object to the hydrogel. The plastic carrier 48 and release coating 50 is removed prior to application of the electrode 10 to the patients' skin.

Figure 4:
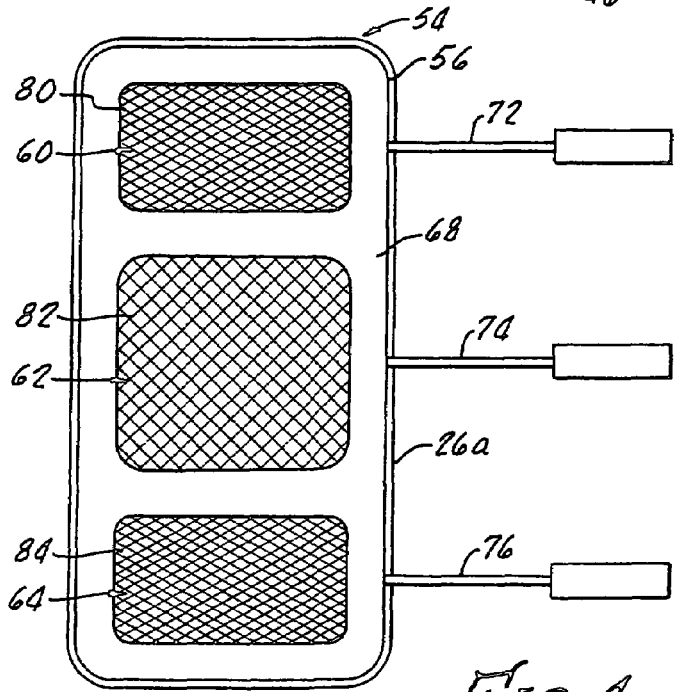
FIG. 4 is an alternative embodiment of the present invention illustrating a plurality of spaced apart conductive flexible members, connectors, and a non-conductive flexible sheet disposed on the conductive member having dimensions greater than the total dimension of the conductive flexible member thereby causing a full overlap thereof by a sheet perimeter.
Figure 5:
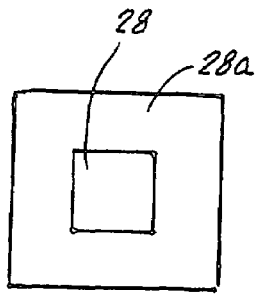
FIG. 5 is a plan view of the central and perimeter adhesive.

Shown in FIG. 4 is another electrode embodiment 54 which includes a conductive flexible member 56 having a plurality of highly conductive ink patterns 60, 62, 64 disposed on a bottom side 68 of the conductive member 56. The conductive ink patterns 60, 62 and 64 may be of various shapes and grid patterns in order to customize the electrical conductivity of the electrode 54 beneath the pattern 60, 62, 64.

The spaced apart pattern 60, 62 and 64 act as separate electrodes and communicate with lead wires 72, 74, 76 respectively, which are attached to a top side (not shown in FIG. 4) of the conductive member 56 as illustrated in FIG. 2 with the description of the electrode embodiment 10.

The advantage of utilizing a common conductive member 56 with spaced apart ink patterns 60, 62, 64 is that this structure provides uniformity of spacing between the independent electrodes. This in effect provides a template to insure proper electrode placement on a patient's skin.

It should be appreciated that, as shown in FIG. 4, the connector 72, 74, 76 are placed over the ink patterns 60, 62, 64. The lead wires 72, 74, 76 can be placed anywhere between the borders 80, 82, 84 of the ink patterns 60, 62, 64 since the current distribution across the electrode gel 44 is independently controlled as hereinabove noted.

Although there has been hereinabove described a specific medical electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A medical electrode comprising:
   a conductive flexible member having a top side and a bottom side;
   a connector in contact with the conductive flexible member for establishing electrical contact with an external apparatus;
   a non-conductive flexible sheet disposed over the conductive flexible member top side, said non-conductive flexible sheet having dimensions greater than said conductive flexible member causing an overlap thereof by a sheet perimeter;
   a central adhesive for bonding said non-conductive flexible sheet to the top side of said conductive flexible member and securing said connector to said conductive flexible member top side;
   a separate perimeter adhesive, of different composition than said central adhesive, disposed about said central adhesive, on the sheet perimeter for sealing of the non-conductive flexible sheet perimeter to a user's skin; and
   a conductive adhesive, disposed on the conductive flexible member bottom side in a spaced apart relationship with said perimeter adhesive, and positioned for adhering the conductive flexible member to the patient's skin.

2. The electrode according to claim 1 wherein said conductive adhesive comprises a conductive hydrogel said central adhesive comprises a hot melt adhesive and said perimeter adhesive comprises a silicone adhesive.

3. A medical electrode comprising:
   a conductive flexible member having a top side and a bottom side;
   a connector in contact with the conductive flexible member for establishing electrical contact with an external apparatus;
   a non-conductive flexible sheet disposed over the conductive flexible member top side, said non-conductive flexible sheet having dimensions greater than said conductive flexible member causing an overlap thereof by a sheet perimeter;
   a central hot melt adhesive for bonding the conductive flexible member to said non-conductive flexible sheet and securing said connector to the conductive flexible member top side;
   a separate silicone perimeter adhesive disposed about the central adhesive, on the sheet perimeter for sealing the non-conductive flexible sheet perimeter to a user's skin; and
   a conductive hydrogel adhesive, disposed on the conductive flexible member bottom side in a spaced apart relationship with said perimeter adhesive, and positioned for adhering the conductive flexible member to a patient's skin.

4. In a medical electrode having:
   a conductive flexible member having a top side and a bottom side;
   a connector in contact with the conductive flexible member top side, for establishing electrical contact wit an external apparatus;
   an adhesive for bonding said non-conductive flexible sheet to the top side of said conductive flexible member and securing said connector to said conductive flexible member top side; and
   a conductive adhesive disposed on the conductive flexible member bottom side for adhering the conductive flexible member to a patient's skin, an improvement comprising:
   a non-conductive flexible sheet disposed over the connector on the conductive flexible member top side, said non-conductive flexible sheet having dimensions greater than said conductive flexible member causing an overlap thereof by a sheet perimeter;
   a central adhesive for bonding said non-conductive flexible sheet to the top side of said conductive flexible member; and
   a separate perimeter adhesive, of different composition than said central adhesive, surrounding said central adhesive, on the sheet perimeter and enabling sealing of the non-conductive flexible sheet perimeter to a user's skin.

5. The electrode according to claim 4 wherein said conductive adhesive comprises a conductive hydrogel said central adhesive comprises a hot melt adhesive and said perimeter adhesive comprises a silicone adhesive.

* * * * *